United States Patent
Biedermann et al.

(10) Patent No.: US 12,096,966 B2
(45) Date of Patent: Sep. 24, 2024

(54) BONE ANCHOR

(71) Applicant: BIEDERMANN TECHNOLOGIES GMBH & CO. KG, Donaueschingen (DE)

(72) Inventors: Timo Biedermann, Trossingen (DE); Markku Biedermann, Key Biscayne, FL (US)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 150 days.

(21) Appl. No.: 17/684,157

(22) Filed: Mar. 1, 2022

(65) Prior Publication Data

US 2022/0280214 A1    Sep. 8, 2022

Related U.S. Application Data (60) Provisional application No. 63/157,107, filed on Mar. 5, 2021.

(30) Foreign Application Priority Data

Mar. 5, 2021 (EP) .................................... 21161042

(51) Int. Cl.
*A61B 17/86* (2006.01)
*A61B 17/88* (2006.01)

(52) U.S. Cl.
CPC ........ *A61B 17/863* (2013.01); *A61B 17/8635* (2013.01); *A61B 17/88* (2013.01); *A61B 2017/8655* (2013.01)

(58) Field of Classification Search
CPC . F16B 25/103; F16B 25/0052; A61B 17/8635
See application file for complete search history.

(56) References Cited

U.S. PATENT DOCUMENTS 3,937,119 A * 2/1976 Ernst .................... F16B 25/0052
                                                        411/311
4,572,875 A * 2/1986 Gutshall ............. F16B 25/0047
                                                        428/585

(Continued)

FOREIGN PATENT DOCUMENTS

CA    2 057 957 A1    6/1992
FR    2 971 138 A1    8/2012

(Continued)

OTHER PUBLICATIONS

Extended European Search Report for Application No. 21161042.3, mailed Aug. 30, 2021, 9 pages.

*Primary Examiner* — David W Bates
(74) *Attorney, Agent, or Firm* — Lewis Roca Rothgerber Christie LLP (57) ABSTRACT

A bone anchor includes a shank having a longitudinal axis, a core, a tip at one end of the core, and a thread forming a helix that extends around the core with a lower flank directed towards the tip and an upper flank directed away from the tip. A recess in a first turn of the thread forms a cutting structure, the recess being defined by first and second surfaces directly connected to one another at an angle. The first and second surfaces are spaced apart from every other turn of the thread above or below the first turn. A majority of the first surface is positioned higher axially than and circumferentially aligned with part of the second surface. At least one of the first or second surfaces extends circumferentially around the shank by a greater distance than an axial height of the at least one surface.

20 Claims, 6 Drawing Sheets

(56) References Cited

U.S. PATENT DOCUMENTS

| | | | | |
|---|---|---|---|---|
| 4,697,969 A * | 10/1987 | Sparkes | ............. | F16B 25/0078 411/421 |
| 4,842,467 A * | 6/1989 | Armstrong | ............ | F16B 35/048 411/386 |
| 4,973,210 A * | 11/1990 | Osborne | ............... | F16B 35/041 411/389 |
| 5,110,245 A * | 5/1992 | Hiroyuki | ............ | F16B 25/0047 411/417 |
| 7,819,905 B2 | 10/2010 | Newcomb et al. | | |
| 10,888,363 B2 | 1/2021 | Greenhalgh et al. | | |
| 2004/0253076 A1 * | 12/2004 | French | ................ | F16B 25/0068 411/417 |
| 2005/0265805 A1 * | 12/2005 | Suzuki | ................ | F16B 25/0021 411/386 |
| 2006/0039775 A1 * | 2/2006 | Mizuno | ............... | F16B 25/0021 411/387.4 |
| 2011/0318137 A1 * | 12/2011 | Chen | ................... | F16B 25/0057 411/387.1 |
| 2013/0039720 A1 * | 2/2013 | Shih | .................... | F16B 25/0047 411/387.4 |
| 2016/0000472 A1 | 1/2016 | Cormier et al. | | |
| 2016/0115989 A1 * | 4/2016 | Hubmann | ........... | F16B 25/0015 411/411 |
| 2016/0131171 A1 * | 5/2016 | Hamada | .................. | F16B 25/00 411/386 |
| 2016/0138639 A1 * | 5/2016 | Fujimoto | ............ | F16B 25/0021 411/386 |
| 2018/0146987 A1 | 5/2018 | Corbin et al. | | |
| 2018/0303529 A1 * | 10/2018 | Zastrozna | ............ | A61B 17/864 |
| 2019/0085887 A1 * | 3/2019 | Su | ......................... | F16B 25/103 |
| 2019/0107137 A1 * | 4/2019 | Su | ......................... | F16B 25/103 |
| 2019/0374269 A1 | 12/2019 | Kiefer et al. | | |
| 2020/0256372 A1 * | 8/2020 | Hsu | ................... | F16B 25/0026 |
| 2021/0102571 A1 * | 4/2021 | Hu | ..................... | F16B 25/0015 |
| 2021/0140462 A1 * | 5/2021 | Shih | ................... | F16B 25/0015 |
| 2021/0190119 A1 * | 6/2021 | Chen | .................. | F16B 25/0073 |

FOREIGN PATENT DOCUMENTS

| | | |
|---|---|---|
| FR | 2 971 413 A1 | 8/2012 |
| FR | 3 000 664 A3 | 7/2014 |

* cited by examiner

BONE ANCHOR

CROSS-REFERENCE TO RELATED APPLICATION(S)

The present application claims priority to and the benefit of U.S. Provisional Patent Application No. 63/157,107, filed Mar. 5, 2021, the contents of which are hereby incorporated by reference in their entirety, and claims priority from European Patent Application EP 21 161 042.3, filed Mar. 5, 2021, the contents of which are hereby incorporated by reference in their entirety.

BACKGROUND

Field

The application relates to a bone anchor of the self-drilling and/or self-tapping type, which is particularly applicable in the field of orthopedic surgery.

Description of Related Art

Various procedures can be used to insert a bone anchor, in particular a bone screw, into bone. For example, in one procedure, a pilot hole is prepared in the bone and an internal thread is tapped in the pilot hole. Thereafter, the bone screw is screwed into the prepared hole. In another procedure, a self-tapping screw is inserted into a pre-drilled pilot hole. In a further procedure, a self-drilling screw is directly inserted into bone without preparing a pilot hole in advance.

A self-drilling bone screw is, for example, known from U.S. Pat. No. 7,819,905 B2. The bone screw includes a screw body centered on a longitudinal axis and having an external thread winding. The bone screw has a head portion at one end of the screw body and a drill point at the other end.

A bone anchor with a shaft that facilitates starting the bone anchor in a proximal surface of the bone is known from US 2016/0000472 A1. The shaft has a first threaded section distal to a proximal head, a second threaded section distal to and adjacent the first threaded section, and a third threaded section distal to and adjacent the second threaded section. The first threaded section has a constant major and minor diameter. The second threaded section has a tapering major and minor diameter. The third threaded section has a tapering major diameter and a constant minor diameter.

US 2018/0146987 A1 describes a spinal fastener with a serrated thread. The serrations reduce the insertion torque, thereby improving ease of insertion, while not compromising pullout strength.

SUMMARY

It is an object of the invention to provide an improved bone anchor of the self-drilling and/or the self-tapping type that facilitates insertion into bone.

According to an embodiment, the bone anchor includes a shank configured to be anchored in bone, the shank having a longitudinal shank axis and including a core and a tip at one end of the core and a thread configured to engage bone. The thread includes at least one turn of a helix around the core, the at least one turn including a lower flank facing towards the tip and an upper flank facing away from the tip, where the shank includes an additional cutting structure with a recess in the turn of the thread, the recess being defined by two adjacent surfaces and being oriented such that a thickness of the thread in an axial direction between the upper flank and the lower flank is reduced along a portion of the turn.

The bone anchor is configured to be inserted into bone without the need to prepare a pilot hole in advance. Hence, the bone anchor can be inserted in one procedural step into the bone. Thereby, the time needed for placing the bone anchor can be significantly reduced. Also, use of fluoroscopy can be reduced.

In an embodiment, the additional cutting structure is at or close to the tip. This permits engagement of the bone safely with the first turn of the thread. Thereby, the shank of the bone anchor can more easily penetrate into the bone. Moreover, the bone anchor can be placed without using a K-wire, any other wire, or an awl.

In a further embodiment, the additional cutting structure is provided at the transition between a tapering part of the thread to a cylindrical part of the thread. By means of this, the insertion torque at the transition of the thread shape from tapering to cylindrical can be reduced when compared to a similar arrangement without an additional cutting structure. This facilitates the further advancement of the bone anchor into bone without additional instruments needed to prepare the screw trajectory.

In a still further embodiment, the additional cutting structure is formed close to the tip and/or at the transition from a conical thread portion to a cylindrical thread portion.

The additional cutting structures are easy to manufacture.

In a method of use, the bone anchor is placed onto the bone, for example, onto the surface of the pedicle of a vertebra, and with, preferably light, hits on the bone anchor, the cortical bone is opened. The additional cutting structure at or close to the tip also reduces the surface that penetrates the bone and assists the thread in engaging the bone with the first thread turn. Then the bone anchor is driven into the bone, wherein the thread is self-tapping. When the bone anchor is advanced into the bone, the additional cutting structure at the transition from a conical thread portion to a cylindrical thread portion further reduces the required insertion torque.

A particular field of application of the bone anchor is orthopedic surgery, more particularly, spine surgery. The bone anchor can be, for example, part of a monoaxial or polyaxial pedicle screw that is configured to connect the vertebra to a spinal rod. However, the bone anchor can also be used in other fields of spine and orthopedic surgery, for example, in connection with additional fixation of interbody cages, bone plates for osteosynthesis, or fixation of joint replacements.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
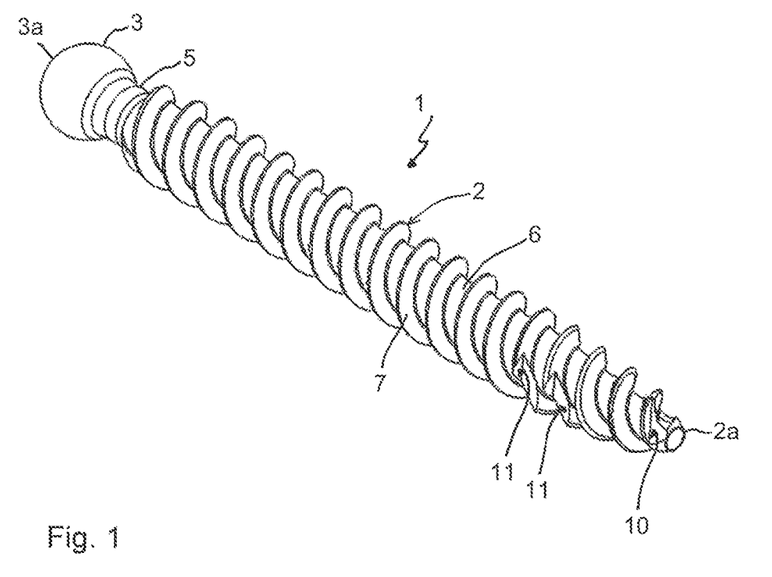
FIG. 1 shows a perspective view from a tip of a bone anchor according to an embodiment.
Figure 2:
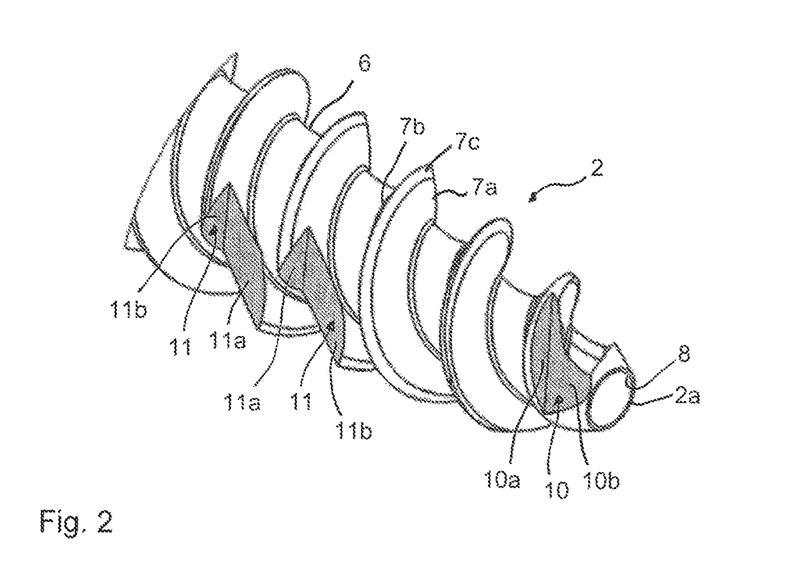
FIG. 2 shows an enlarged portion of a region adjacent to the tip of the bone anchor of FIG. 1.
Figure 3:
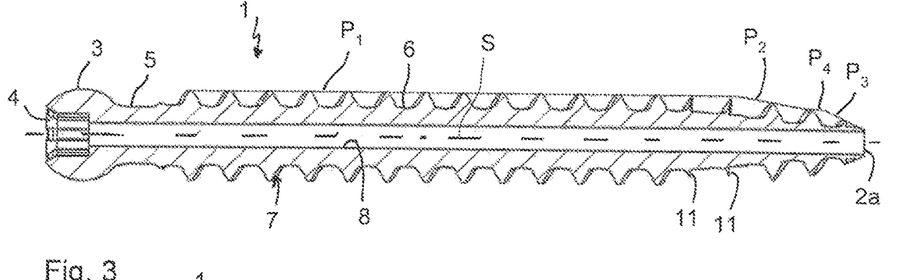
FIG. 3 shows a cross-sectional view of the bone anchor of FIGS. 1 and 2, the cross-section taken in a longitudinal direction and through the shank axis.

Referring to FIGS. 1 to 8, a bone anchor 1 according to an embodiment of the invention is in the form of a bone screw. The bone anchor includes a shank 2 configured to engage bone. The shank 2 has a tip 2a at one free end that is configured to enter the bone first. The tip may be blunt or sharp. At an opposite second end of the shank 2, a head 3 may be formed that may have a spherical outer surface portion and a free end surface 3a. More specifically, the head 3 may have the shape of a spherical segment having a substantially flat end surface. Further, as shown in FIG. 3, an engagement recess 4 may be provided in the free end surface 3a of the head 3 for engagement with a drive tool. Adjacent to the head 3, a reduced diameter neck section 5 may be formed. The head 3 may be assembled with a receiving part (not shown) of a polyaxial bone anchor, where the receiving part has an accommodation space having a seat for the head 3 that enables the head 3 to pivot in the seat similar to a ball and socket joint. Furthermore, the receiving part may have a recess for receiving a spinal rod and a locking assembly for locking the head and the rod in the receiving part.

The shank 2 includes a core 6 and a thread 7 winding in a helix around the core 6 in a plurality of turns. In the embodiment, the thread 7 extends from the tip 2a up to the neck 5. In greater detail, the thread 7 includes a lower flank 7a facing towards the tip 2a, an upper flank 7b facing towards the head 3, and a crest 7c between the lower and upper flanks. The cross-section of the thread may be substantially V-shaped with a rounded or flat crest 7c. The thread pitch and the geometry of the thread 7 may be such that there is a gap between the thread turns on the core 6. Specifically, the thread shape and thread pitch is such that the thread is adapted to engage bone.

Figure 4:
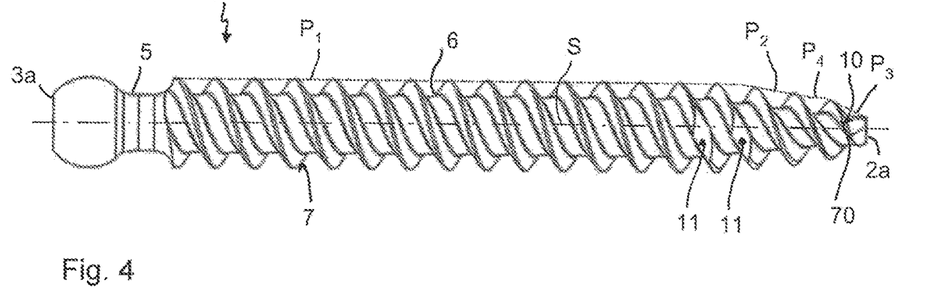
FIG. 4 shows a side view of the bone anchor of FIGS. 1 to 3.
Figure 5:
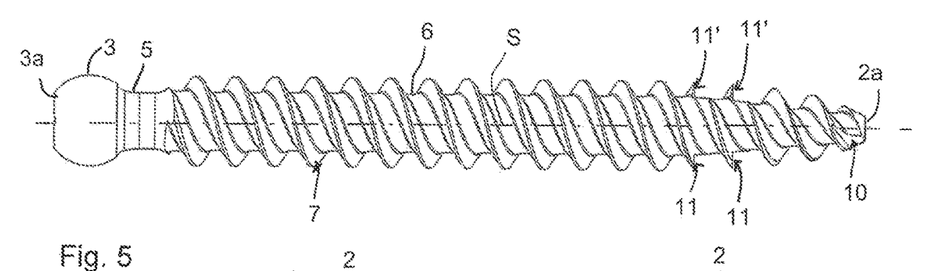
FIG. 5 shows a side view of the bone anchor of FIGS. 1 to 4, where the view is rotated by 90° with respect to the side view shown in FIG. 4.
Figure 6A:
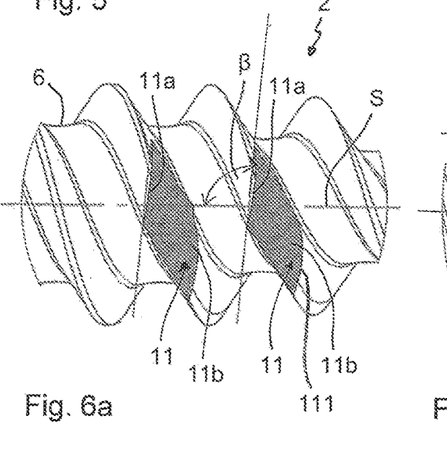
FIG. 6a shows an enlarged portion of FIG. 4 in a region of additional cutting structures.
Figure 6B:
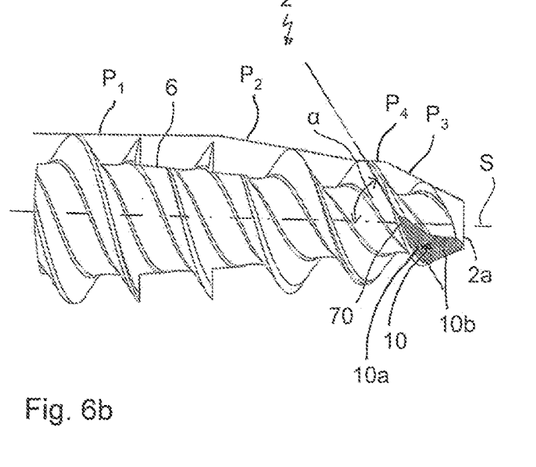
FIG. 6b shows an enlarged portion of FIG. 5 in a region adjacent to the tip.

As best seen in FIGS. 3, 4 and 6, there is a first portion $P_1$ of the thread 7 adjacent to the neck 5 which is cylindrical and which extends over an axial length that may be more than half of the axial length of the shank 2. In the first portion $P_1$, the outside diameter of the core 6 and the outside diameter of the thread 7 are constant. Adjacent to the cylindrical first portion $P_1$ in a direction towards the tip 2a, a second portion $P_2$ of the thread 7 tapers towards the tip 2a, preferably conically. In the second portion $P_2$, the outside diameter of the core 6 decreases towards the tip 2a. Adjacent to the tip 2a, a third portion $P_3$ is formed in which the outside diameter of the core 6 and preferably also the outside diameter of the thread 7 decrease towards the tip 2a, preferably in a conical manner with a cone angle that may be greater than that of the second portion $P_2$. Between the second portion $P_2$ and the third portion $P_3$, a fourth portion $P_4$ may be formed which may be cylindrical.

It shall be noted that, while the pitch and the cross-section of the thread 7 remains substantially the same in the embodiment shown, there may be other embodiments where the pitch varies along the length of the shank and/or wherein the shape of the thread varies along the length of the shank. Moreover, in the embodiment shown, the bone screw has a dual thread, or two separate threads that wind around the core. Other embodiments may have more or less than two threads that wind around the core, e.g., the thread can also be arranged as a single thread. The specific thread shape, the pitch, the number of threads, etc., are parameters that may depend on the type of bone into which the anchor is to be inserted and/or on the purpose of the bone anchor. The shank may also have thread free portions, i.e., the thread 7 may be present only in a portion or portions of the shank.

At the first thread turn adjacent to the tip 2a, an additional cutting structure 10 is formed that is configured to cut into bone additionally to the thread. The additional cutting structure 10 includes a first substantially flat surface 10a and a second substantially flat surface 10b that join each other and thereby form an angle that may be between 80° and 100°, and preferably about 90° or more preferably 90°. The corner formed by the joining surfaces may be slightly rounded, which may result from manufacturing. Hence, the additional cutting structure 10 is defined by a recess provided at the first thread turn at a spatially discrete or confined position in the direction of the helical thread turn. In other words, the recess extends only along a portion of the thread turn. In greater detail, the recess extends over a length of the helical thread turn that is less than one half of the length of the thread turn, preferably less than ⅓ of the length of the thread turn, and more preferably about ¼ or less of the length of the thread turn. The recess extends axially into the lower flank 7a and into a portion of the core 6. An orientation of the recess with respect to the shank axis S is such that the first substantially flat surface 10a forms an angle α of about 50 to 70°, preferably about 65°, with the shank axis S, as depicted schematically in FIG. 6b. Hence, the recess forming the additional cutting structure 10 is oriented with respect to the direction in which the bone anchor is inserted into bone at an obtuse angle. A line defined by the corner of the joining surfaces defining the recess may be inclined with respect to the shank axis when seen in a plane parallel to the shank axis. By the recess, a portion of the lower flank 7a is cut away. More generally, by the recess, an axial thickness or width of the thread turn along a portion of the thread turn in the direction of the helix is reduced. This may result in a reduced surface at the tip for entering the bone surface, and a sharper cutting edge of the thread in this region to engage the bone for further advancement. A contour or a cross-section of the two surfaces may be asymmetrical, in particular, with respect to each other. The second surface 10b is oriented substantially parallel to the shank axis S. As can also be seen in FIG. 6b, a portion 70 of the crest 7c of the turn of the thread in which the additional cutting structure 10 is formed may also be reduced in width such that it is sharpened. The angle α which the first substantially flat surface 10a forms with the shank axis S may depend on the cross-section of the thread, and can be selected to obtain an additional cutting effect. The additional cutting structure 10 which is close to the tip 2a facilitates the penetration of the cortical bone. The penetration may be facilitated in several ways, that may include the reduction of the insertion force in the axial direction and/or easier rotational engagement of the screw with the bone.

Figure 7:
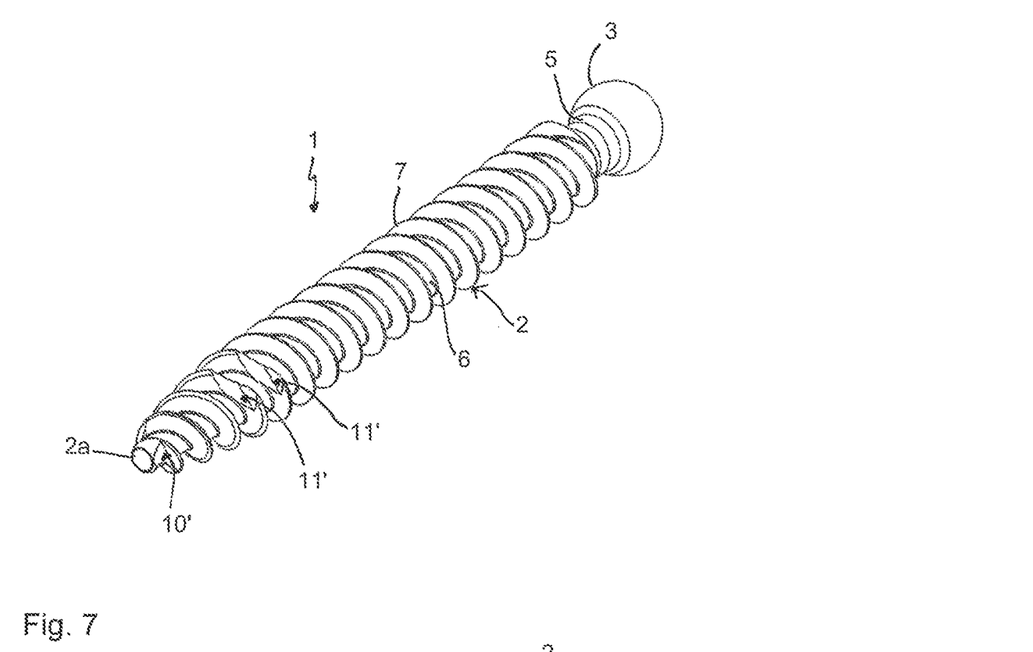
FIG. 7 shows a perspective view of the bone anchor of FIGS. 1 to 6b seen from the tip, wherein the view is rotated by 180° compared to the view shown in FIG. 1.
Figure 8:
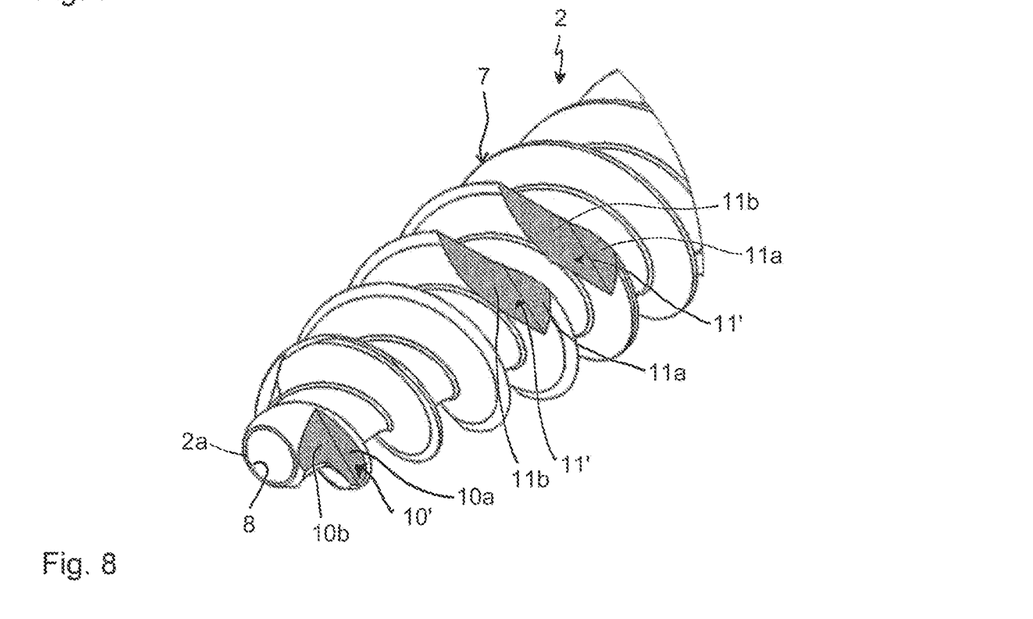
FIG. 8 shows an enlarged portion of the bone anchor of FIG. 7 in a region adjacent to the tip.

Referring to FIGS. 7 and 8, corresponding to the additional cutting structure 10, a second additional cutting structure 10' of the same type may be provided at a position offset from the first additional cutting structure 10 by 180°.

Referring again to FIGS. 1 to 6b, further additional cutting structures 11 of the same type as the additional cutting structure 10 may be provided on thread turns at a distance from the tip 2a. The further additional cutting structures 11 have a first substantially flat surface 11a and a second substantially flat surface 11b that join each other at an angle between 80° and 100°, preferably about 90° and more preferably 90°. Moreover, a front edge 111 of the second surface 11b which faces towards the tip 2a lies substantially in a plane that is tangential to the surface of the core 6. By the two substantially flat surfaces 11a, 11b, a recess is defined in the thread 7 that facilitates cutting into bone when the bone anchor is further advanced into bone. The recess is located at a spatially discrete or confined position in a direction of the helical thread turn, and extends along a length of the helical thread turn that is less than one half of the length of the thread turn, preferably less than ⅓ of the length of the thread turn, and more preferably about ¼ or less of the length of the thread turn. The recess extends axially into the lower flank 7a and through the crest 7c into the upper flank 7b, and optionally into a portion of the core 6. A line defined by the corner of the joining surfaces defining the recess may be inclined with respect to the shank axis when seen in a plane parallel to the shank axis. More generally, by the recess, an axial thickness or width of the thread turn or of a portion of the thread turn in the direction of the helix is reduced. This may result in a sharper cutting edge of the thread in this region. A required torque for screwing the bone anchor further into the bone is reduced.

As depicted in FIGS. 7 and 8, associated with each further additional cutting structure 11, a second further additional cutting structure 11' is provided on the respective thread turn offset from the further additional cutting structure 11 by 180°.

Different from the additional cutting structure 10, 10' at the tip, the recess of the additional cutting structure 11, 11' is oriented with respect to the shank axis S such that the first substantially flat surface 11a forms an angle β of about 80° to 110° with the shank axis S, preferably about 95° as schematically depicted in FIG. 6a. Thereby, the crest 7c is partially interrupted and partially thinned, thus providing a sharp cutting edge.

In the embodiment shown, two such further additional cutting structures 11, 11' are provided on subsequent turns of the thread 7 but one additional cutting structure 11, 11' may be sufficient. The two further additional cutting structures 11, 11' are at an axial position corresponding to a region of transition between the tapering second portion $P_2$ and the cylindrical first portion $P_1$. In greater detail, at least one of the additional cutting structures 11, 11' is located substantially in the tapering second portion $P_2$, close to or partially within the cylindrical first portion $P_1$. By means of this, advancement of the bone anchor into bone at the transition between the tapering portion $P_2$ and the cylindrical portion $P_1$ can be more easily facilitated by additional cutting. The additional cutting structure 11, 11' reduces the torque necessary to advance the transition from the conical portion to the cylindrical portion. The two additional cutting structures 11 on subsequent thread turns are located at the same circumferential position. Relative to the additional cutting structure 10, 10' which is close to the tip 2a, the further additional cutting structures 11, 11' may be slightly offset with respect to their circumferential positions, as can be seen in particular in FIGS. 1 and 2. It shall be noted that the number of further additional cutting structures 11, 11' can also be less than two or more than two. It may also be possible to provide such additional cutting structures 11, 11' at every second or third thread turn.

The first and second substantially planar surfaces 10a, 10b, 11a, 11b of the additional cutting structures 10, 10', 11, 11' may have irregular contours. This results from manufacturing when the recess is cut in the thread and the core.

Between the additional cutting structure 10 and the additional cutting structure 11, at least one, and preferably two to three or more, full turns of the thread without an additional cutting structure may be present.

As can be seen in particular in FIG. 3, the entire bone anchor may optionally be cannulated. The bone anchor may define a channel 8 extending fully from the free end surface 3a of the head 3 through the shank 2 up to the tip 2a. The channel 8 is preferably coaxial with the shank axis S and has a circular cross-section. An inner diameter of the channel may be substantially constant over the length of the channel. However, the inner diameter may also vary along the length, and/or the cross-section may have shapes other than circular. In a further embodiment (not shown), the shank may be fenestrated, i.e., the shank may have one or a plurality of laterally extending openings that connect the channel 8 with the outside of the bone anchor.

The bone anchor may be made of any bio-compatible material, preferably however, of titanium or stainless steel or of any other bio-compatible metal or metal alloy or plastic material. For a bio-compatible alloy, a NiTi alloy, for example Nitinol, may be used. Other materials that can also be used may be magnesium or magnesium alloys. Biocompatible plastic materials that can be used may be, for example, polyether ether ketone (PEEK) or poly-L-lactide acid (PLLA).

Figure 9:
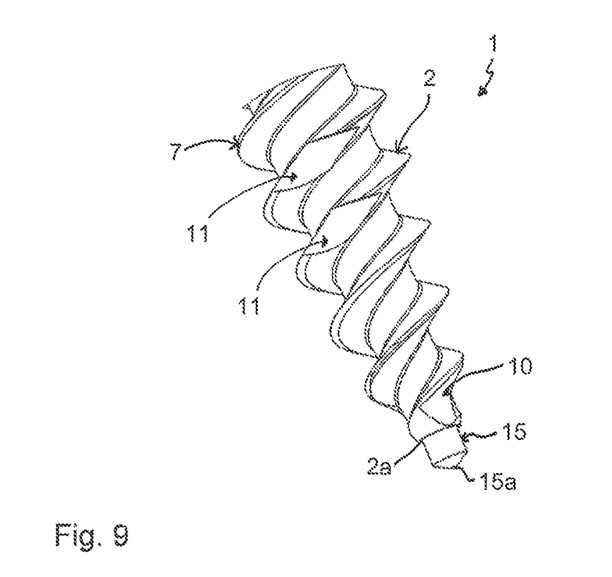
FIG. 9 shows a perspective view of an enlarged portion of the bone anchor of FIGS. 1 to 8 in a region adjacent to the tip, where a wire is guided through the bone anchor and projects out of the tip.

In a modified embodiment, as shown in FIG. 9, a wire 15 may extend through the channel 8 and project out of the tip 2a. The wire may have a tip 15a and may serve for identifying the insertion location of the bone anchor and/or facilitating the first step of penetration into bone.

Figure 10:
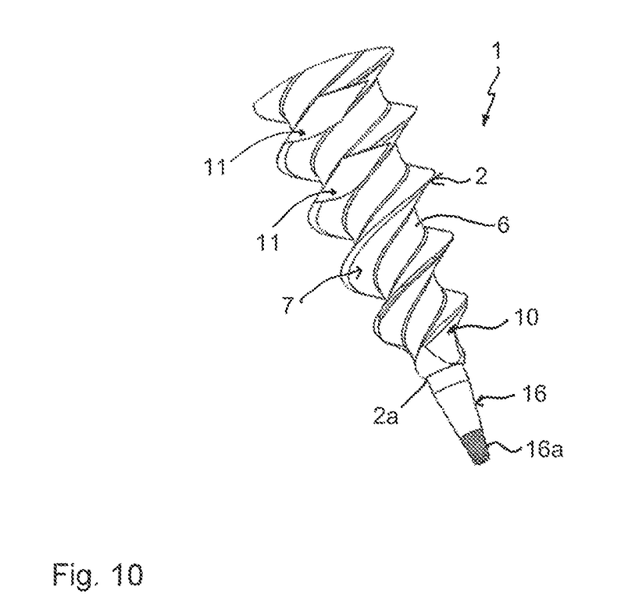
FIG. 10 shows a perspective view of an enlarged portion of the bone anchor of FIGS. 1 to 8 in a region adjacent to the tip, where a sensor is guided through the bone anchor and projects out of the tip.

Alternatively, as shown in FIG. 10, a sensor device 16 may be guided through the channel 8, such that a tip with a sensor portion 16a projects out of the tip 2a of the bone anchor. The sensor device may be configured to sense respective characteristics, such as, for example, a density of the bone, the position of the screw, or may be configured to perform neuro-monitoring. Any other suitable sensor may also be conceivable.

Figures 11, 12:
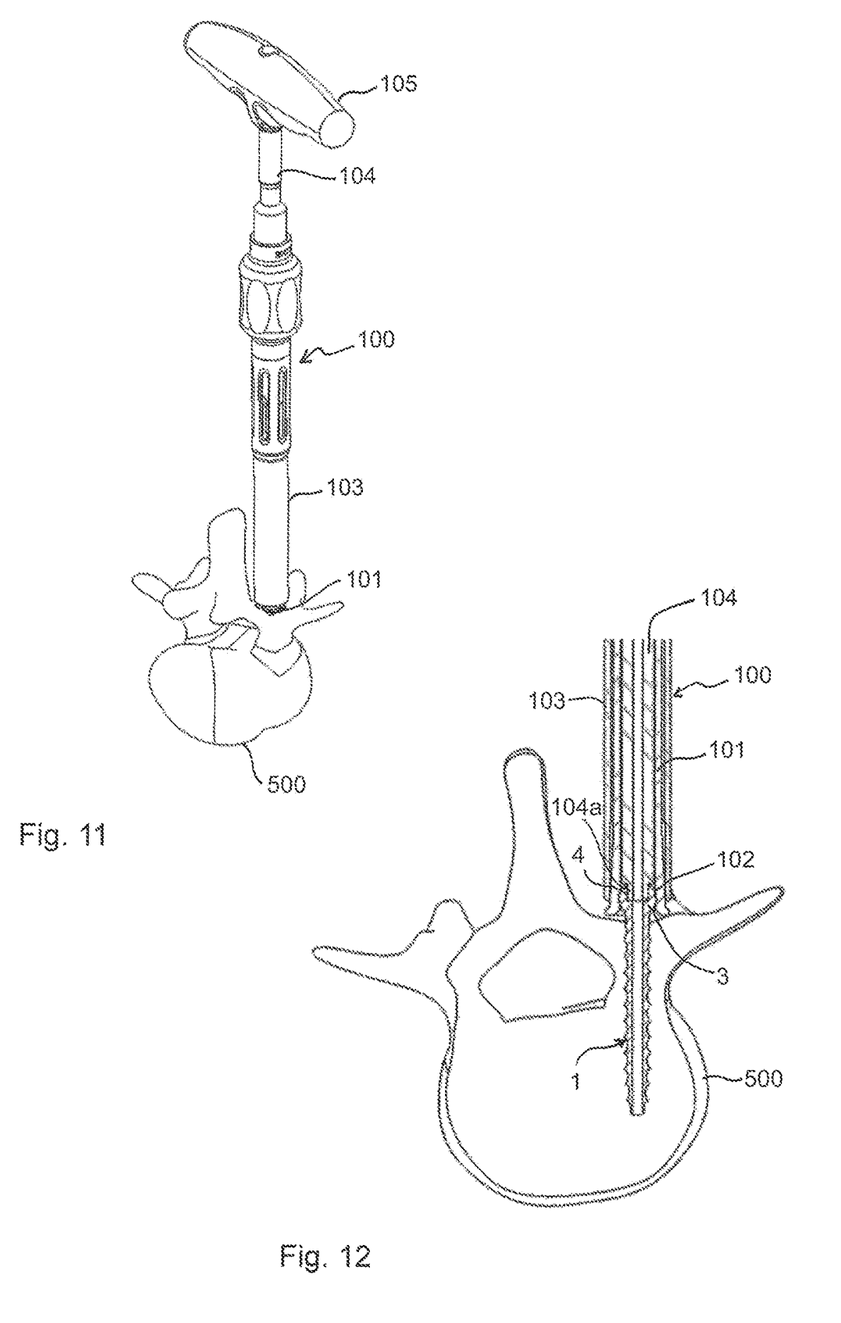
FIG. 11 shows a perspective view of a vertebra and an instrument for inserting the bone anchor of FIGS. 1 to 8 into a pedicle of the vertebra.
FIG. 12 shows a cross-sectional view of a vertebra with inserted bone anchor according to FIGS. 1 to 8 and a portion of the instrument of FIG. 11 attached thereto.

Referring to FIGS. 11 and 12, an instrument 100 for inserting the bone anchor 1 may include a holding sleeve 101 with a fork-shaped front portion and a seat 102 for receiving the head 3 therein. An outer clamping sleeve 103 is displaceable with respect to the holding sleeve 101, from a retracted position in which the head 3 can be received in the seat 102 and removed therefrom, to an advanced position in which the outer sleeve 103 clamps the fork-shaped front portion of the holding sleeve 101 to lock the head 3 in the seat 102. A cannulated drive tool 104 is configured to extend through the holding sleeve 101, and a front portion 104a of the drive tool 104 is configured to engage the recess 4 in the head of the bone anchor 1. The drive tool 104 may have a handle portion 105 at its free outer end.

An example of use is explained, referring to FIGS. 11 and 12. The bone anchor 1 is attached to the instrument by engaging the head 3 with the holding sleeve 101 and locking the head 3 in the seat 102 with the outer sleeve 103. Then, the drive tool 104 is inserted into the holding sleeve 101 and engages the head of the bone anchor. The bone anchor is then driven into bone, in the particular example, into a pedicle of a vertebra 500. When the tip 2a engages the cortical bone, the additional cutting structures 10, 10' that are provided on the first thread turn facilitate the penetration of the screw into the bone and the engagement of the thread 7 with the bone. Thus, the thread cuts in bone already with the first thread turn. When the bone anchor 1 is further driven into the bone, at the transition of the conical second portion $P_2$ to the cylindrical first portion $P_1$ of the bone anchor, the required insertion torque increases. By means of the further additional cutting structures 11, 11', the required torque is reduced so that the insertion of the bone anchor is more easily facilitated. When the bone anchor is fully driven into the bone, the clamping of the head 3 is released by retracting the outer sleeve 103 and removing the instrument 100. Subsequently the head 3 of the bone anchor can be connected, for example, to a receiving part of a polyaxial bone anchoring device. Usually at least two bone anchors are inserted into the pedicles of adjacent vertebrae, and the receiving parts of the corresponding polyaxial bone anchoring devices are connected through a rod.

Figure 13:
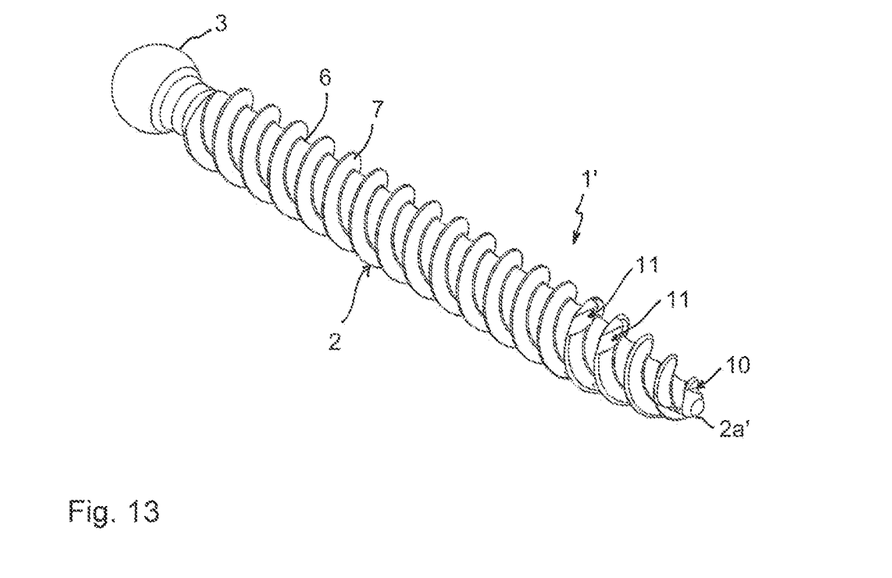
FIG. 13 shows a perspective view from a tip of a bone anchor according to a modified embodiment.
Figure 14:
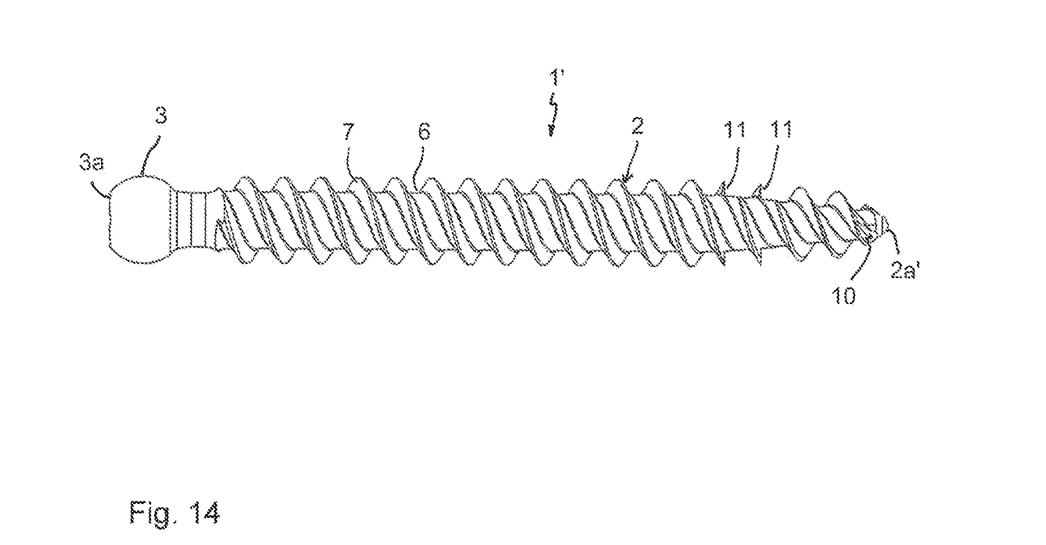
FIG. 14 shows a side view of the bone anchor of FIG. 13.

Referring to FIGS. 13 and 14, a modified embodiment of the bone anchor is shown. The bone anchor 1' is a solid body without a channel extending therethrough. The tip 2a' is closed and may be sharpened. In a still further modified embodiment, the bone anchor defines an internal channel extending from the free end surface 3a of the head 3 up to a distance from the tip, which is closed. In such a still further modified embodiment, lateral openings from the channel to the outside may be provided that allow, for example, injected bone cement to exit to the surrounding bone material.

Further modifications may also be possible without departing from the spirit and scope of the invention. The features of the embodiments shown and described can also be combined to produce a variety of further embodiments. Moreover, the head can be omitted, and a suitable drive structure can be provided at the shank. The bone anchor may have only one or more additional cutting structures close to the tip, or may have one or more additional cutting structures at the transition from a tapering portion of the shank to a cylindrical portion of the shank. While two additional cuttings structures offset by 180° on one thread turn are shown, in other embodiments, one single additional cutting structure on one thread turn may be sufficient, or three or more additional cutting structures spaced apart at regular distances may be provided.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchor comprising a shank configured to be anchored in bone, the shank having a longitudinal axis and comprising:

a core;

a tip at one end of the core; and a thread configured to engage bone, the thread forming a helix that extends around the core and having a lower flank that is directed towards the tip and an upper flank above the lower flank that is directed away from the tip;

wherein a recess in a first turn of the thread forms a cutting structure, the recess being defined by a first surface and a second surface that is directly connected to the first surface, wherein the second surface extends axially downwardly from the first surface at an angle to the first surface, and wherein the first and second surfaces are spaced apart from every other portion of the thread above or below the first turn; and wherein a majority of the first surface is circumferentially aligned with at least part of the second surface, wherein both the first and second surfaces extend circumferentially around the longitudinal axis, and wherein at least one of the first or second surfaces extends circumferentially around the longitudinal axis by a greater distance than a height of the at least one surface measured in a direction of the longitudinal axis.

2. The bone anchor of claim 1, wherein the first and second surfaces are substantially planar.

3. The bone anchor of claim 1, wherein the angle formed between the first and second surfaces is between 80° and 100°.

4. The bone anchor of claim 1, wherein a line that extends along a corner formed between the first and second surfaces extends at an angle relative to the longitudinal axis.

5. The bone anchor of claim 1, wherein the thread further comprises a crest between the lower flank and the upper flank, and wherein the recess extends at least from the lower flank up to the crest.

6. The bone anchor of claim 1, wherein the recess extends circumferentially around the shank for less than ½ of a complete turn of the thread.

7. The bone anchor of claim 1, wherein the cutting structure is a first cutting structure, and wherein a second cutting structure that is spaced apart from the first cutting structure is further provided on the first turn.

8. The bone anchor of claim 1, wherein the cutting structure is formed at a first turn of the thread closest to the tip.

9. The bone anchor of claim 1, wherein a first portion of the thread is cylindrical and a second portion of the thread between the first portion and the tip is tapered, and wherein the cutting structure is formed at or close to a transition between the first and second portions.

10. The bone anchor of claim 9, further comprising a third portion of the thread closest to the tip that is tapered, and a fourth portion of the thread between the second and third portions that is cylindrical.

11. The bone anchor of claim 1, wherein the cutting structure is a first cutting structure, and wherein a second cutting structure is formed on a portion of the thread that is axially adjacent to the first turn and at substantially a same circumferential position as the first cutting structure.

12. The bone anchor of claim 1, wherein an outer surface of the shank is free from axial and/or helical grooves.

13. The bone anchor of claim 1, wherein the shank is cannulated and open at the tip to facilitate guiding of a wire or a sensor device through the shank and out of the tip.

14. The bone anchor of claim 1, wherein the shank is closed at the tip.

15. The bone anchor of claim 1, wherein an angle formed between the first surface and the longitudinal axis is between 50° and 80° when the cutting structure is formed on a turn of the thread that is adjacent to the tip, and is between 80° and 110° when the cutting structure is formed on a turn of the thread that is farther away from the tip.

16. The bone anchor of claim 1, wherein the recess reduces an axial thickness of the thread in a region of the cutting structure.

17. The bone anchor of claim 1, wherein at least part of the recess extends into the core.

18. A method of implanting a bone anchor into bone, the bone anchor comprising a shank having a longitudinal axis and comprising a core, a tip at one end of the core, and a thread configured to engage the bone, the thread forming a helix that extends around the core and having a lower flank that is directed towards the tip and an upper flank above the lower flank that is directed away from the tip, wherein a recess in a first turn of the thread forms a cutting structure, the recess being defined by a first surface and a second surface that is directly connected to the first surface, wherein the second surface extends axially downwardly from the first surface at an angle to the first surface, wherein the first and second surfaces are spaced apart from every other portion of the thread above or below the first turn, wherein a majority of the first surface is circumferentially aligned with at least part of the second surface, wherein both the first and second surfaces extend circumferentially around the longitudinal axis, and wherein at least one of the first or second surfaces extends circumferentially around the longitudinal axis by a greater distance than a height of the at least one surface measured in a direction of the longitudinal axis, the method comprising:

engaging the tip of the shank against a bone without a pre-formed pilot hole;

advancing the shank into the bone with the cutting structure facilitating insertion.

19. The method of claim 18, further comprising attaching a receiving part of a bone anchoring device to the bone anchor.

20. The method of claim 18, further comprising inserting a guide wire or a sensor device through the bone anchor prior to engaging the tip of the shank against the bone, and removing the guide wire or sensor after advancing the shank into the bone.

* * * * *